(12) United States Patent
Lee et al.

(10) Patent No.: US 8,133,985 B2
(45) Date of Patent: Mar. 13, 2012

(54) PEPTIDE NUCLEIC ACIDS CONJUGATED WITH MULTI-AMINE LINKERS AND NUCLEIC ACID DETECTING DEVICE USING THE SAME

(75) Inventors: Hyunil Lee, Daejeon (KR); Hee Kyung Park, Daejeon (KR); Bong Ho Um, Daejeon (KR); Serka Kim, Daejeon (KR); Jae Jin Choi, Daejeon (KR); Jung Hyun Min, Daejeon (KR); Hye Yeon Kim, Daejeon (KR)

(73) Assignee: Panagene Inc. (KR)

( * ) Notice: Subject to any disclaimer, the term of this patent is extended or adjusted under 35 U.S.C. 154(b) by 237 days.

(21) Appl. No.: 12/300,235

(22) PCT Filed: Dec. 14, 2007

(86) PCT No.: PCT/KR2007/006553
§ 371 (c)(1),
(2), (4) Date: Aug. 17, 2009

(87) PCT Pub. No.: WO2008/072933
PCT Pub. Date: Jun. 19, 2008

(65) Prior Publication Data
US 2009/0312197 A1    Dec. 17, 2009

(30) Foreign Application Priority Data

Dec. 15, 2006  (KR) ............... 10-2006-0128938
Dec. 14, 2007  (KR) ............... 10-2007-0130798

(51) Int. Cl.
*C07K 2/00* (2006.01)
*C07K 1/00* (2006.01)
*C40B 80/00* (2006.01)
*C40B 40/06* (2006.01)

(52) U.S. Cl. ........ 536/23.1; 435/6.1; 514/1.1; 514/44 R; 977/754; 506/39; 506/42

(58) Field of Classification Search .................. 506/33, 506/35, 39, 42; 435/6.1; 514/1.1, 44 R; 977/754
See application file for complete search history.

(56) References Cited

U.S. PATENT DOCUMENTS

2003/0077635 A1 * 4/2003 Lohse ............................ 435/6
* cited by examiner

*Primary Examiner* — Christopher M Gross
*Assistant Examiner* — Jeremy C Flinders
(74) *Attorney, Agent, or Firm* — Cantor Colburn LLP

(57) ABSTRACT

The present invention relates to a peptide nucleic acid (PNA) conjugated with multi-amine linkers, and a method to prepare the same and utilization thereof. More specifically, the method is characterized by conjugating monomers having multi-amine functionality sequentially at a PNA terminal, and effectively immobilizing the PNA conjugated with multi-amine linkers on a solid surface. A PNA array prepared using the PNA conjugated with multi-amine linkers exhibits improved sensitivity and specificity of signals for detecting target nucleic acids as compared to a PNA array using PNA probes having only one amine group. The PNA conjugated with multi-amine linkers can be utilized in nucleic acid detecting devices or kits for gene diagnosis such as PNA microarrays, PNA chips, PNA field-effect transistors and impedance detectors.

13 Claims, 10 Drawing Sheets

[Figure 1]
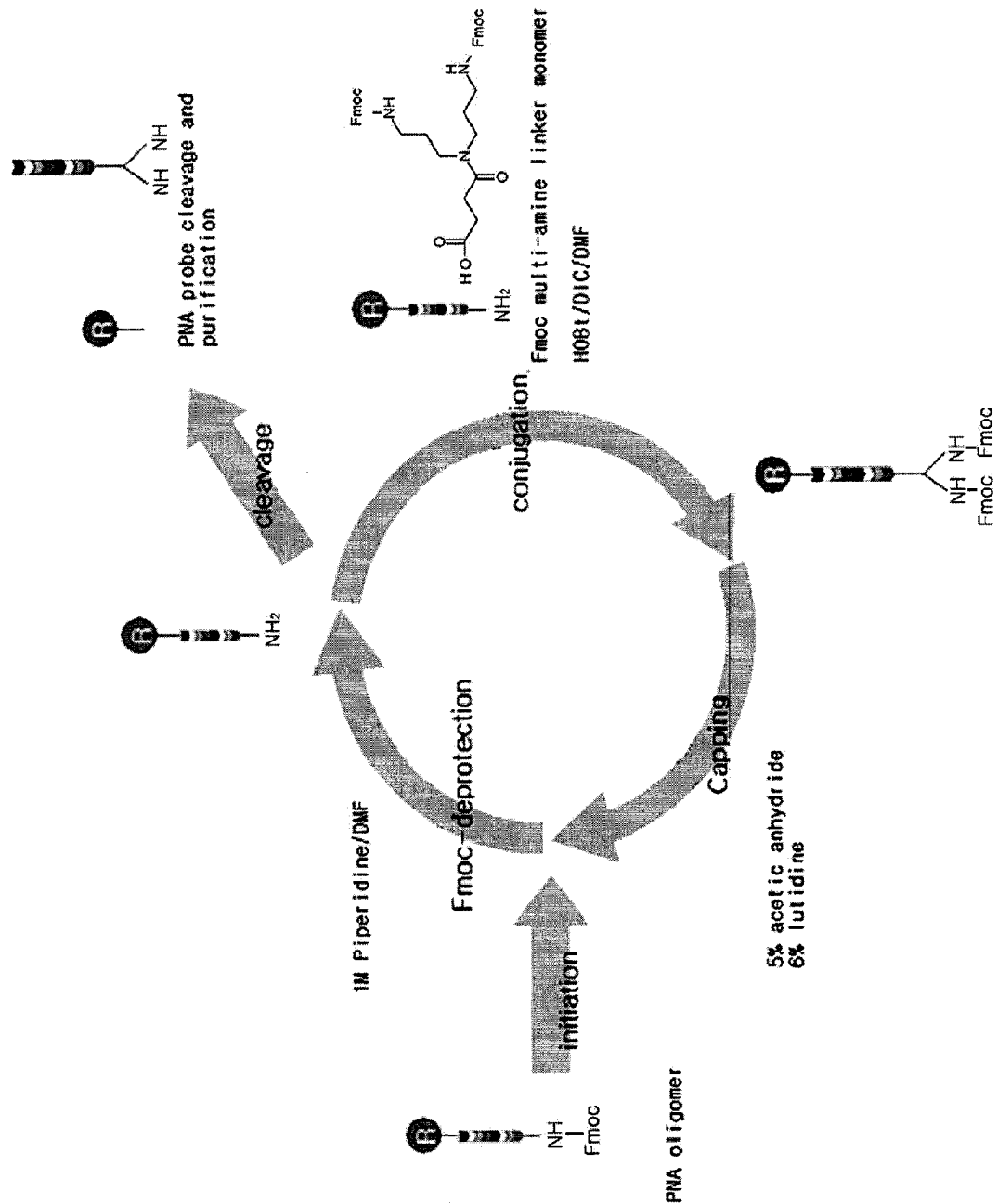

[Figure 2]
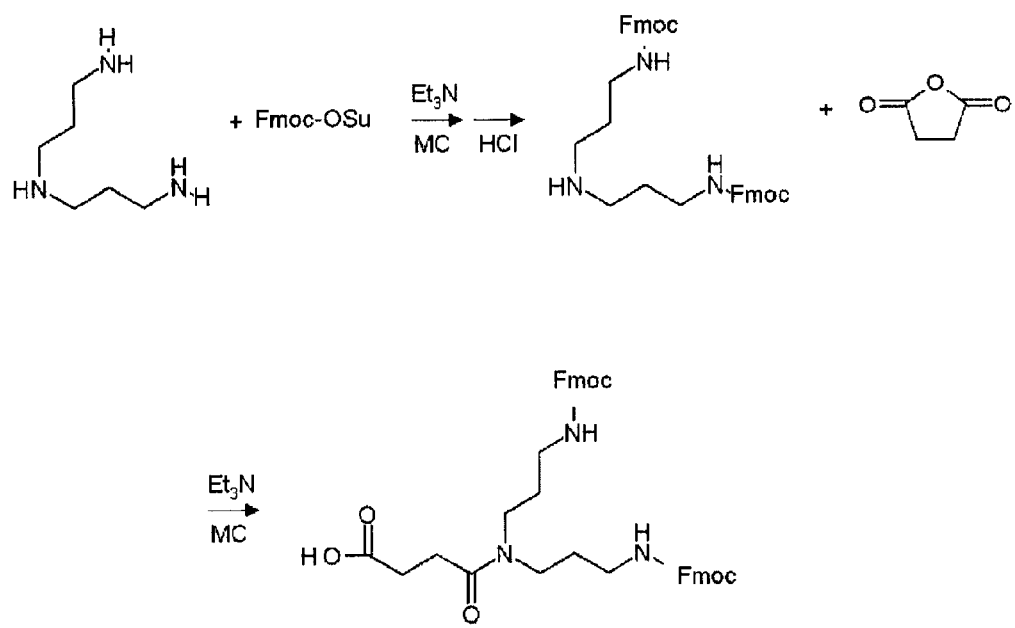

[Figure 3]
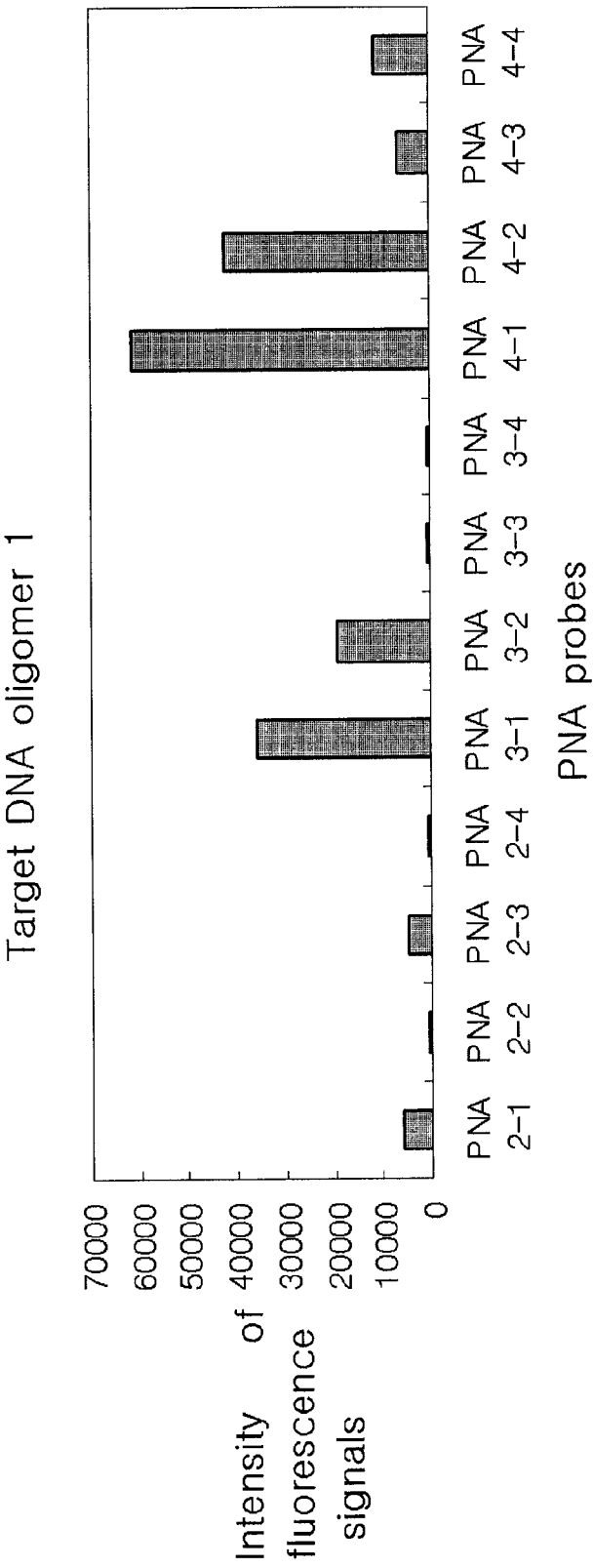

[Figure 4]
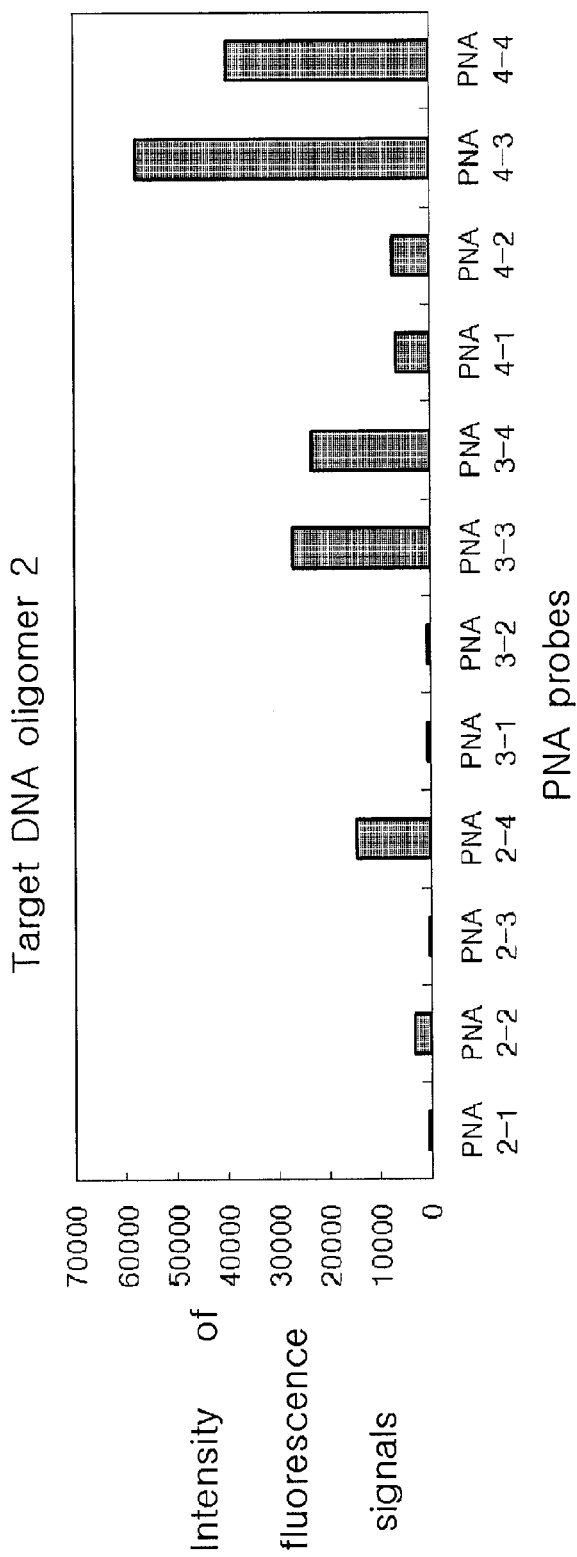

[Figure 5]
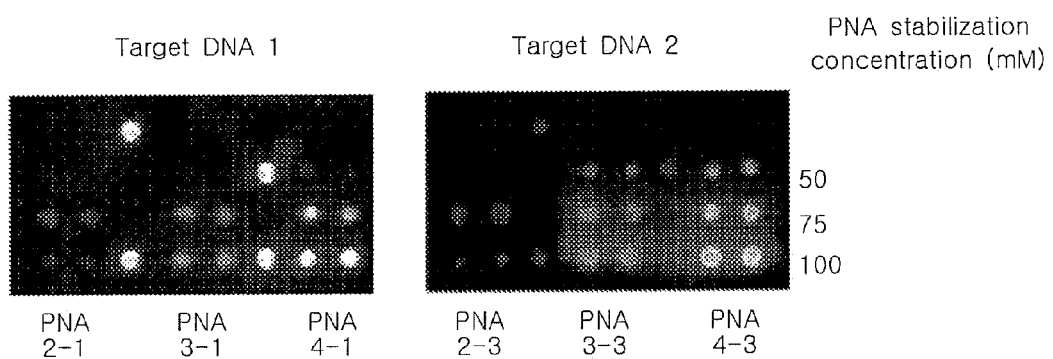

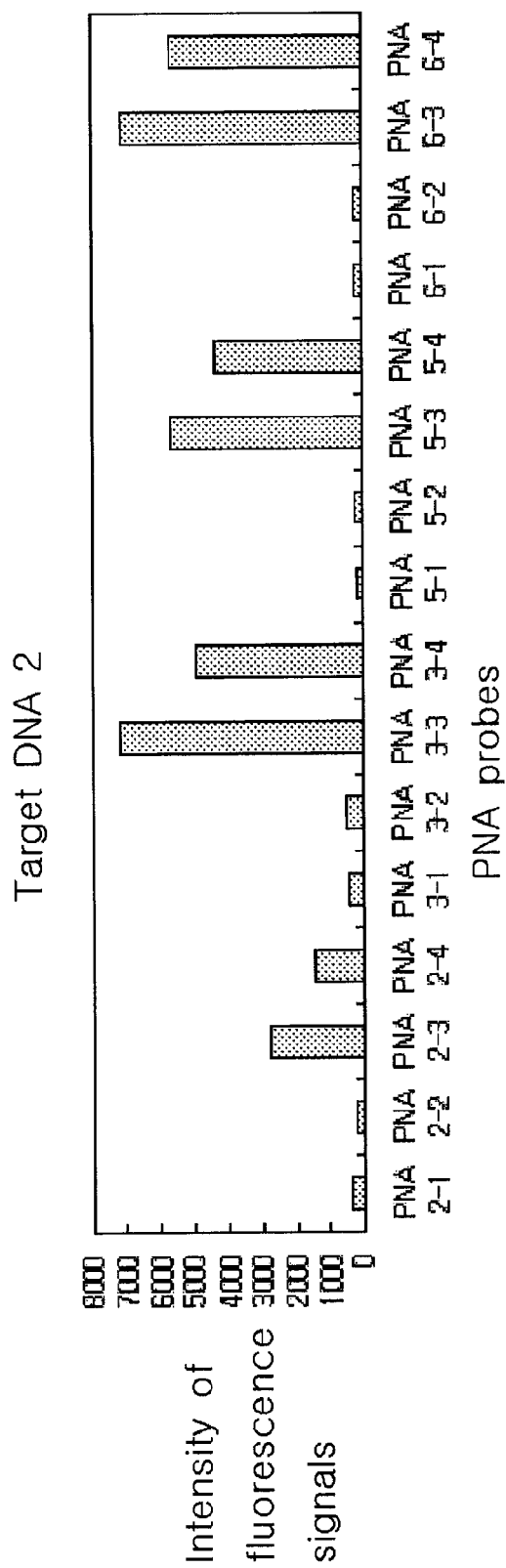
[Figure 6]

[Figure 7]
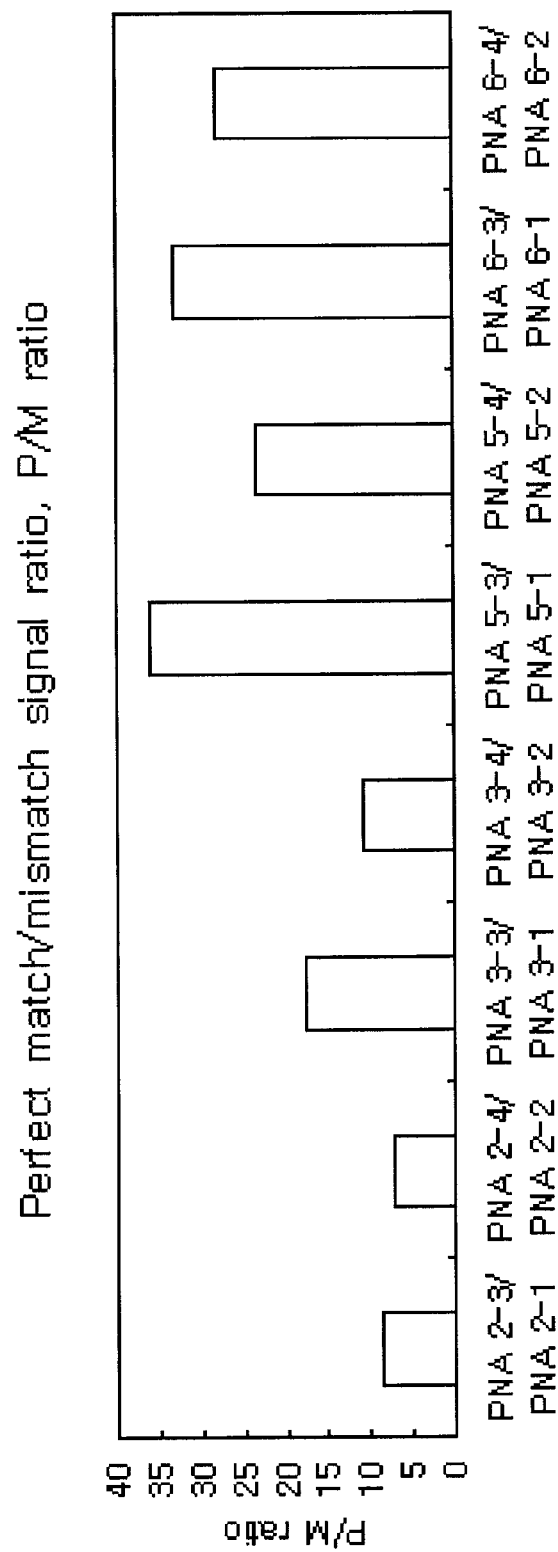

[Figure 8]
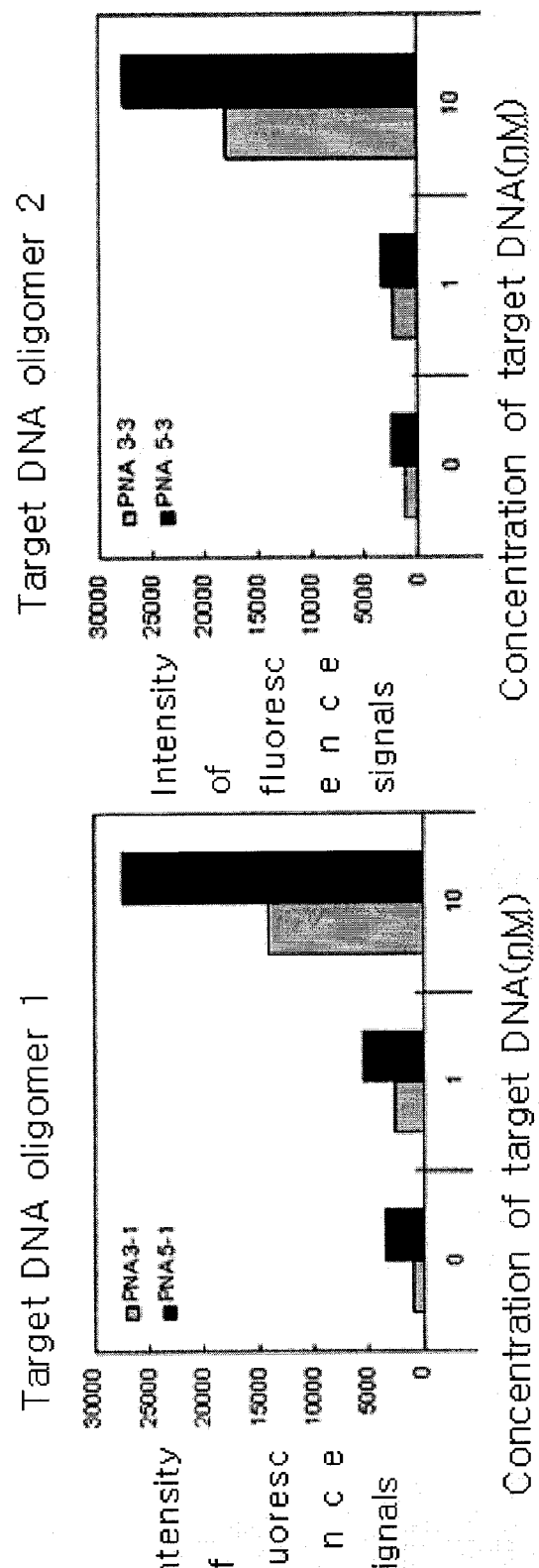

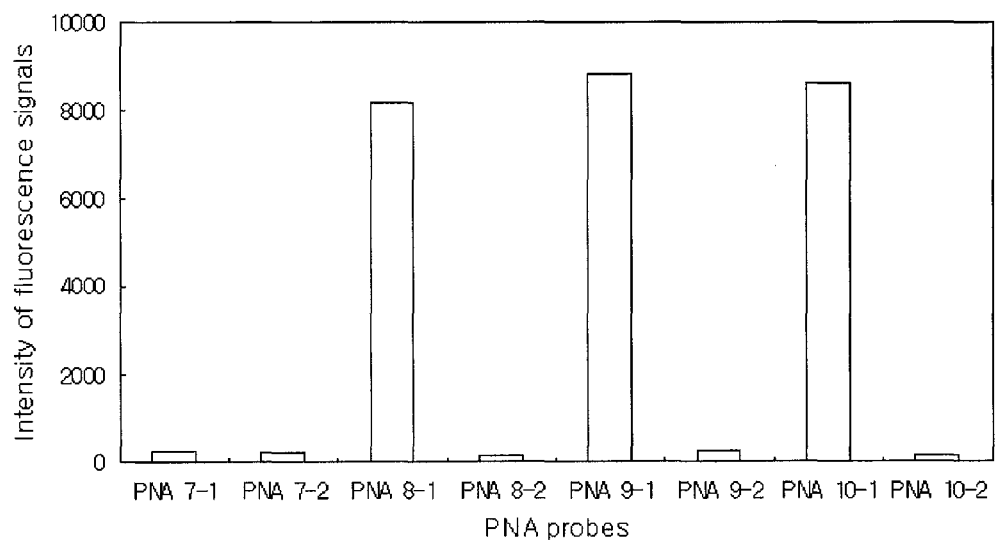
[Figure 9]

[Figure 10]
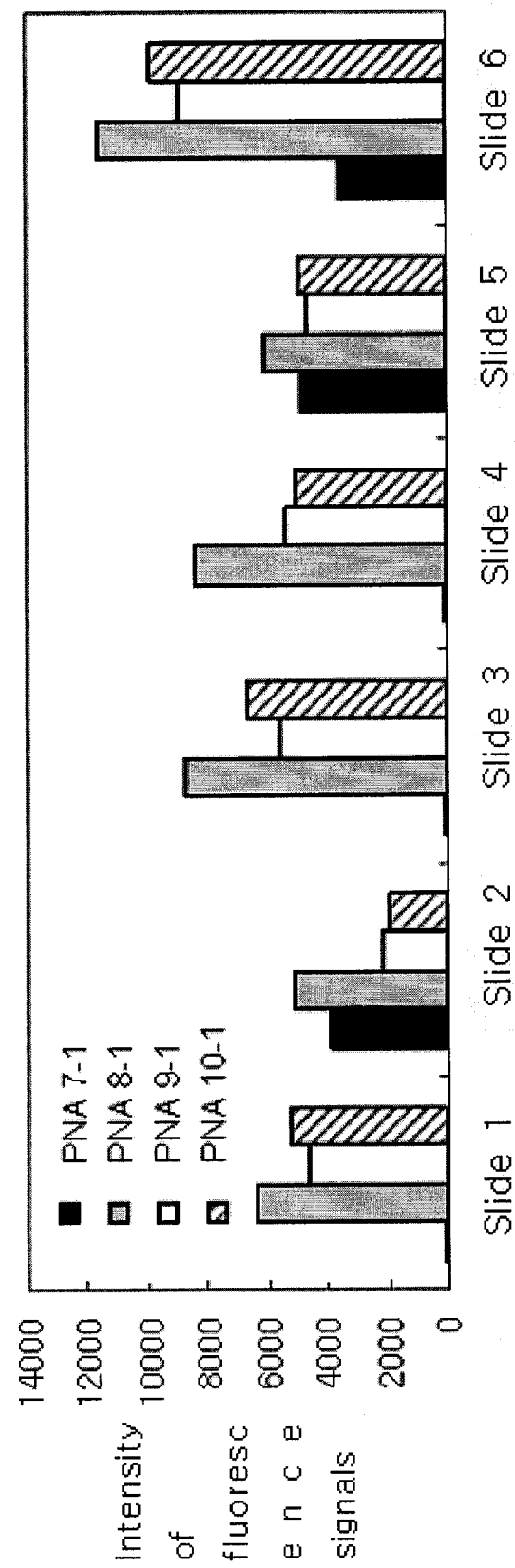

```
SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Target DNA oligomer 1*.   *Target DNA oligomer
      1 was designed to specifically hybridize with PNA oligomers 2-1,
      2-2, 3-1, 3-2, 4-1, 4-2, 5-1, 5-2, 6-1 and 6-2 of Examples 2 to 6.

<400> SEQUENCE: 1
ctctaataaa agcaaacagc ctg                                             23

<210> SEQ ID NO 2
<211> LENGTH: 21
<212> TYPE: DNA
<213> ORGANISM: Artificial Sequence
<220> FEATURE:
<223> OTHER INFORMATION: Target DNA oligomer 2**.  ** Target DNA
      oligomer 2 was designed to specifically hybridize with PNA
      oligomers 2-3, 2-4, 3-3, 3-4, 4-3, 4-4, 5-3, 5-4, 6-3 and 6-4.

<400> SEQUENCE: 2
ctgtaataaa taaacagcct g                                               21

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
tgcaagtcga acggtaacag                                                 20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tgcgacgtta tgcggtatta                                                 20
```

PEPTIDE NUCLEIC ACIDS CONJUGATED WITH MULTI-AMINE LINKERS AND NUCLEIC ACID DETECTING DEVICE USING THE SAME

TECHNICAL FIELD

The present invention relates to peptide nucleic acid probes conjugated with multi-amine linkers at one end, a method to immobilize the same on solid surface, and a device to detect nucleic acid sequence and a kit for gene diagnosis comprising peptide nucleic acids immobilized on solid surface.

BACKGROUND ART

Peptide nucleic acids (hereinafter, referred to as 'PNA'), a kind of artificial DNA analog, were firstly reported wherein the nucleic bases are linked by peptide bonds instead of phosphate bonds (Nielsen P E, Egholm M, Berg R H, Buchardt O, "Sequence-selective recognition of DNA by strand displacement with a thymine-substituted polyamide", Science 1991, Vol. 254, pp 1497-1500). PNA are not found in nature and synthesized through chemical methods. PNA undergo hybridization reaction with natural nucleic acids having the complementary base sequence to form a double strand. In case of having identical number of the nucleobases, a PNA/DNA double strand is more stable than a DNA/DNA double strand, and a PNA/RNA double strand is more stable than a DNA/RNA double strand. Most commonly used backbone of PNA is N-(2-aminoethyl)glycine repeatedly linked by amide bond, which is electrically neutral differently from that of natural nucleic acids with negative charge.

Four nucleobases in PNA occupy almost the same space as nucleobases of DNA, having almost same distance between nucleobases as that of natural nucleic acids. PNA are more stable chemically and biologically than natural nucleic acids, because they are not decomposed by a nuclease or a protease. The stability of a PNA/DNA or PNA/RNA double strand is not affected by salt concentration because PNA is electrically neutral. Due to these properties, PNA can better recognize the complimentary nucleotide sequence than natural nucleic acids, so that PNA can be applied for diagnosis and other biological or medical purposes.

When a nucleotide sequence is recognized or detected in a homogeneous solution by using a probe of known base sequence, typically one target sequence is recognized at one time. It is difficult to detect more than a few sequences at the same time by using fluorescent dyes of different colors. On the other hand, a lot more number of sequences can be detected concurrently when probes are immobilized on a solid surface. DNA microarrays wherein several hundred thousands of probes are arranged in two dimensions have been already put into practical use. PNA microarrays or PNA chips employing PNA probes instead of DNA probes have been also known (Brandt O, Hoheisel J D, "Peptide nucleic acids on microarrays and other biosensors", Trends in Biotechnology 2004, Vol. 22, pp 617-622). A method to simultaneously examine a plurality of targets by immobilizing PNA probes on distinguishable microbeads or microspheres of several micrometer size has been reported (Rockenbauer E, Petersen K H, Vogel U, Bolund L, Kølvraa S, Nielsen K V, Nexeø BA, "SNP genotyping using microsphere-linked PNA and flow cytometric detection", Cytometry Part A 2005, Vol. 64A, pp 80-86). Fluorescence is widely used to determine whether or not hybridization reaction occurs between probes and complementary nucleotide sequences, whereas electrical detection methods also known by using a field-effect transistor with PNA immobilized on silicon semiconductor or silicon nanowire [F. Uslu et al. "Labelfree fully electronic nucleic acid detection system based on a field-effect transistor device", Biosensors and Bioelectronics 2004, Vol. 19, pp 1723-1731; J. Hahm and C. M. Lieber, "Direct ultrasensitive electrical detection of DNA and DNA sequence variations using nanowire nanosensors", Nano Letters 2004, Vol. 4, pp 51-54]. A device to recognize nucleotide sequence by detecting impedance change has been also reported [A. Macanovic et al. "Impedance-based detection of DNA sequences using a silicon transducer with PNA as the probe layer", Nucleic Acids Research 2004, Vol. 32, e20].

Since the mass of the probe is changed after hybridization of the target nucleic acid, the nucleotide sequence can be detected by measuring the mechanical change resulted therefrom. The resonance frequency of a microcantilever or a surface acoustic wave (SAW) sensor changes after hybridization of DNA or RNA, so that it can be use for detection. Microcantilevers and SAW sensors using PNA have been reported [S. Manalis and T. Burg, U.S. Pat. No. 7,282,329 "Suspended microchannel detectors"; P. Warthoe and S. Iben, US Patent Application Publication 2004/0072208 A1 "Surface acoustic wave sensors and method for detecting target analytes"].

In such a device or method of multiplex analysis using PNA probes, the PNA probes needs to be immobilized on solid surface. Covalent bonds formed by a chemical reaction is more stable than physical attraction, and thus frequently selected as a method of immoblilization. Covalent bonds generated by aldehyde-amine, carboxylic acid-amine, or epoxide-amine reaction are widely used in biochips such as PNA microarrays, DNA microarrays and protein micorarrays (M. Schena, Microarray analysis, A. John Wiley & Sons, Inc., 2003, pp 95-120). In order to immobilize PNA on a glass surface, a glass surface is subject to silylation by an organosilane substance having aldehyde, amine or epoxy group in order to expose the functional group on the glass surface. N-terminal amine group of a PNA probe is reacted with the exposed functional group to form a covalent bond.

By using a functional group of high reactivity, the efficiency of immobilization of the probe can be enhanced. At a terminal of DNA or PNA probes, a highly active functional group such as hydrazide may be used (S. Raddatz et al., "Hydrazide oligonucleotides: new chemical modification for chip array attachment and conjugation", *Nucleic Acids Research*, 2002, Vol. 30, pp 4793-4802). According to this method, a biochip with higher sensitivity can be obtained by enhancing immobilization efficiency of DNA or PNA probes to a surface. The immobilizing efficiency of probes can be also enhanced by increasing the reactivity on a surface. According to this method, a highly active linker is chemically bonded to a simple amine or aldehyde functional group immobilized on a solid surface to expose activated ester or isothiocyanate, which would then react with DNA or PNA probes. However, such a functional group of high reactivity at a probe terminal or on solid surface is easily degraded and is difficult to keep active.

DISCLOSURE

Technical Problem

The object of the present invention is to provide PNA probes conjugated with multi-amine linkers, and a method for preparing the same.

Another object of the present invention is to provide a method to immobilize the said PNA probes conjugated with multi-amine linkers on a functionalized surface with high efficiency.

Still another object of the present invention is to provide a nucleotide sequence detecting device or a kit for gene diagnosis which is manufactured by immobilizing the said PNA probes conjugated with multi-amine linkers on a solid surface made of a functionalized plastic substrate, silica, silicon semiconductor, magnetic molecules, nylon, polymers, thin film, cellulose or nitrocellulose, as well as a functionalized glass substrate.

Technical Solution

In order to achieve the objects mentioned above, the present invention relates to PNA conjugated with multi-amine linkers, and a synthetic method for the PNA, and its utilization. More specifically, the present invention is characterized by conjugating multiple times at N-terminal of PNA a linker consisting of a monomer having multi-amine functionality to prepare PNA having multi-amine functionality, enhancing the immobilization efficiency on a solid substrate having electrophilic functional group on the surface, and improving intensity and sensitivity of detection signal of the target nucleic acid or gene that is detected by the PNA probes.

In addition, the present invention provides a device and a kit for gene diagnosis having enhanced sensitivity and specificity, using the PNA conjugated with multi-amine linkers.

The PNA conjugated with multi-amine linkers according to the present invention is represented by Chemical Formula (1):

[Chemical Formula 1]

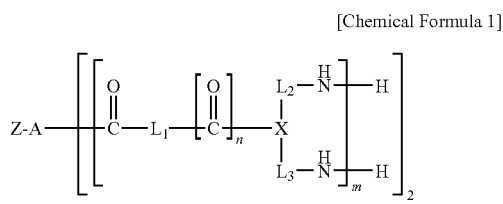

In the Formula, Z represents a PNA oligomer having 8~30 nucleobases; A is bonded to N-terminal of the PNA oligomer and represent a chemical bond or

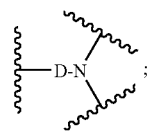

wherein D represents alkylene having 8~200 carbon atoms, and one or more carbon atoms of the alkylene may be substituted by nitrogen, oxygen or carbonyl;

$L_1$, $L_2$ and $L_3$ independently represent a chemical bond, or an alkylene having 1~10 carbon atom(s), and the carbon atoms in alkylene may be further substituted by one or more oxygen atom(s);

X represents CH or N;

m represents an integer from 2 to 10; and n is 0 or 1.

DESCRIPTION OF DRAWINGS

FIG. 1 is a schematic of a process for conjugating a monomer having multi-amine functionality with PNA (wherein, R is resin).

FIG. 2 shows synthetic process for a monomer (Chemical Formula 3-3) to be conjugated with PNA according to Example 1.

FIGS. 3 to 5 compare the immobilization efficiency of PNA probes with different number of amine functional groups by means of PNA array.

FIGS. 6 and 7 compare the immobilization efficiency and P/M ratio of multi-amine linkers by means of PNA array.

FIG. 8 compares the signal intensity of symmetric multi-amine linkers with asymmetric multi-amine linkers by means of PNA array.

FIGS. 9 and 10 compare the degree of immobilization with respect to different slide surfaces by means of PNA array (Slide 1: an epoxy slide, Slide 2: an aldehyde slide (from Company A), Slide 3: an epoxy slide (from Company A), Slide 4: an amine slide coated with butanediol diglycidyl ether (from Company B), Slide 5: an amine slide coated with 1,4-phenylene diisothiocyanate (from Company C), Slide 6: a slide coated with activated ester (from Company D), immobilization probes: PNA 7-1, PNA 8-1, PNA 9-1, PNA 10-1)

BEST MODE

Other and further objects, features and advantages of the invention will appear more fully from the following description.

DETAILED DESCRIPTION OF THE PREFERRED EMBODIMENT

The PNA having the structure represented by following chemical formula, reported by Buchardt, Nielsen, Egholm, Berg et al. (Denmark) in 1991 for the first time (wherein N-(2-aminoethyl)glycine is linked via amide bond) can be employed in the present invention.

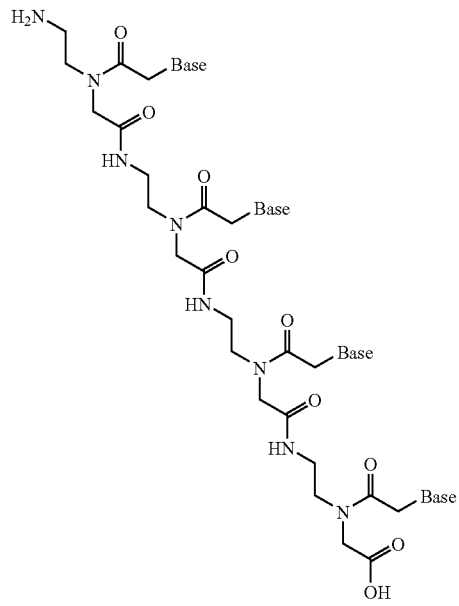

PNA

Though the PNA with the backbone of polymerized N-(2-aminoethyl)glycine is most commonly used, the PNA's represented by one of the following chemical formulas have been also known [P. E. Nielsen and M. Egholm "An Introduction to PNA" in P. E. Nielsen (Ed.) "Peptide Nucleic Acids: Protocols and Applications" 2nd Ed. Page 9 (Horizon Bioscience, (2004)), and can be used for the present invention.

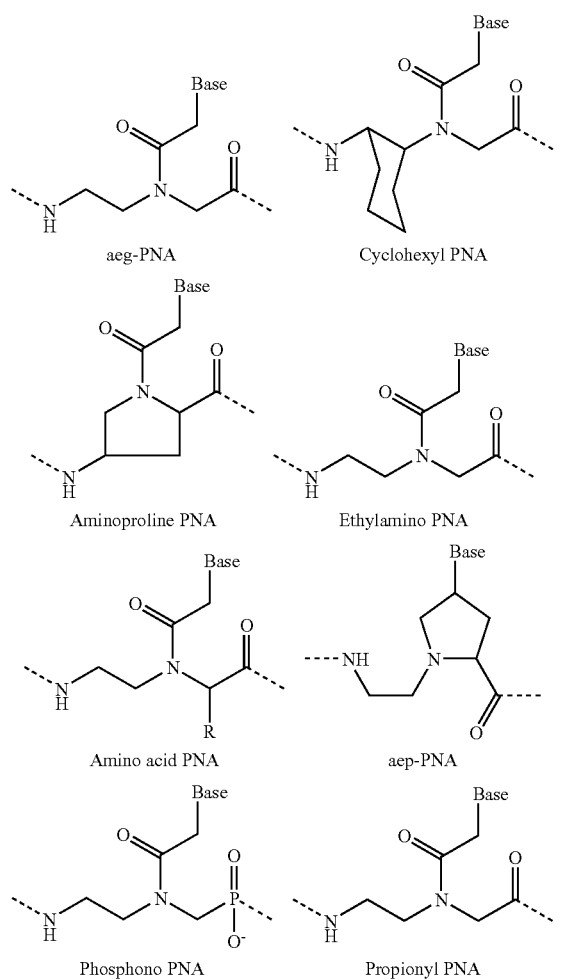

A PNA probe immobilized on a solid surface in order to detect nucleotide sequence or gene preferably comprises 8~30 nucleobases. When a PNA probe is immobilized too close to the solid surface, hybridization with the target gene may be hindered. Thus, spacers may be inserted between the solid surface and the PNA probe in order to immobilize the PNA probe at a certain distance from the solid surface. For example, one or more spacer(s) represented by one of the following chemical formulas may be linked via amide bond at the N-terminal of a PNA probe.

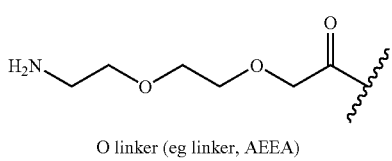

O linker (eg linker, AEEA)

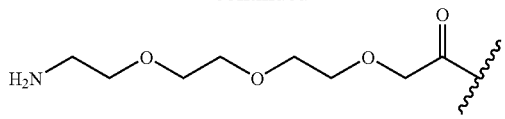

AEEEA linker

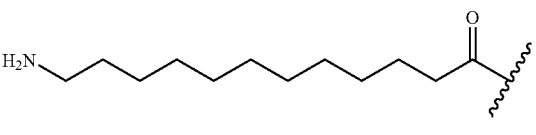

$C_{12}$—NH2 linker

The PNA conjugated with multi-amine linkers according to the invention is represented by Chemical Formula (1):

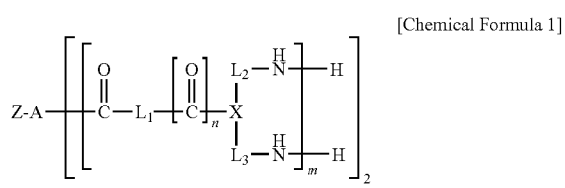

[Chemical Formula 1]

wherein, Z, A, $L_1$, $L_2$, $L_3$, X, m and n are defined as above.

As shown in Chemical Formula (1), a spacer

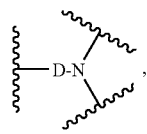

[wherein D represents alkylene having 8~200 carbon atoms, and one or more carbon atoms of the alkylene may be substituted by nitrogen, oxygen or carbonyl] is linked to N-terminal of the PNA oligomer to immobilize it at a certain distance from the solid surface. The spacers can be exemplified as following structures, but are not limited thereto.

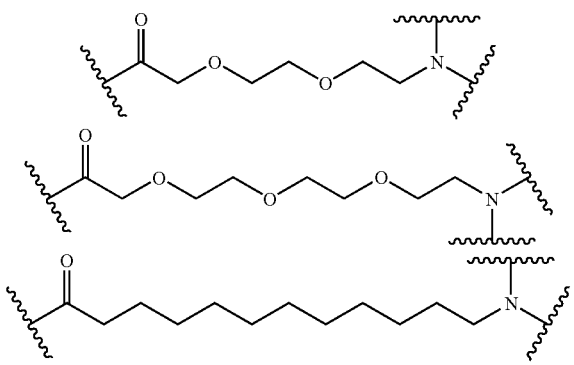

Preferably in the PNA conjugated with multi-amine linkers of Chemical Formula (1), $L_1$, $L_2$ and $L_3$ independently represent a chemical bond, or —$CH_2$—, —$CH_2CH_2$—, —$CH_2CH_2CH_2$— or —$CH_2CH_2CH_2CH_2$—, X represents CH or N, m represents an integer from 2 to 7, and n is 0 or 1.

Specific examples of the moiety excluding

Z-A—⁄⁄⁄ in Chemical Formula (1) include the multi-amine linkers represented by one of Chemical Formulas (1-1) to (1-4), but are not limited thereto.

[Chemical Formula 1-1]

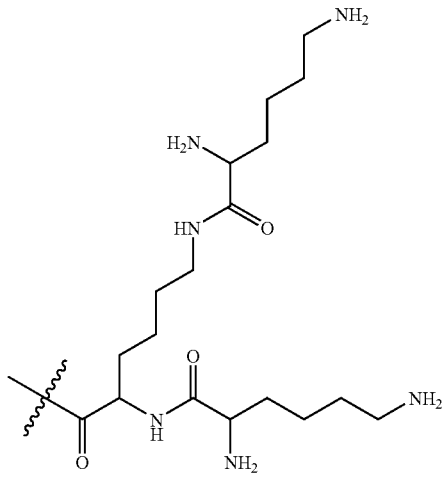

[Chemical Formula 1-2]

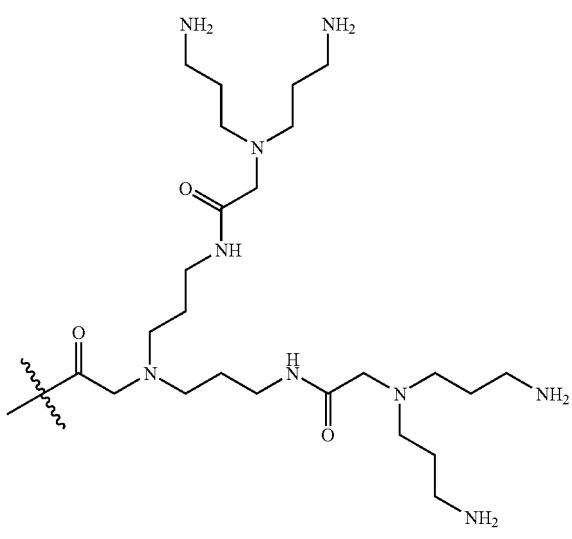

[Chemical Formula 1-3]

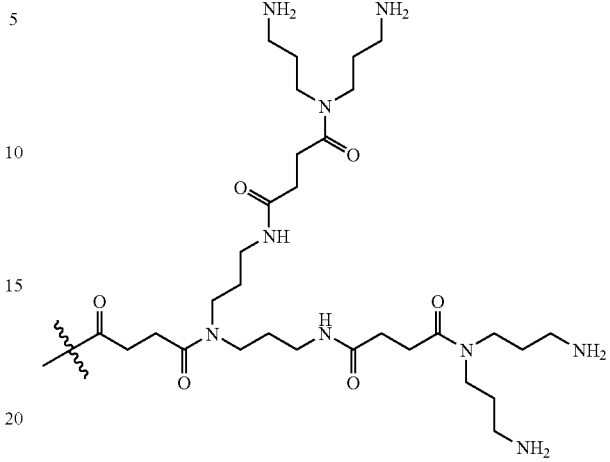

[Chemical Formula 1-4]

Each of Chemical Formulas (1-1) to (1-3) comprises 4 amine functional groups whereas Chemical Formula (1-4) comprises 8 amine functional groups. Chemical Formula (1-2) and (1-3) have symmetric multi-amine groups with four amine functional groups equidistant from a branch point, whereas Chemical Formula (1-1) comprises asymmetric multi-amine groups with four amine functional groups non-equidistant from a branch point.

The PNA conjugated with multi-amine linkers represented by Chemical Formula (1) according to the present invention is characterized in that it is prepared by reacting a monomer having multi-amine functionality represented by Chemical Formula (3) with a PNA oligomer derivative represented by Chemical Formula (2) twice or more up to ten times, sequentially.

[Chemical Formula 2]

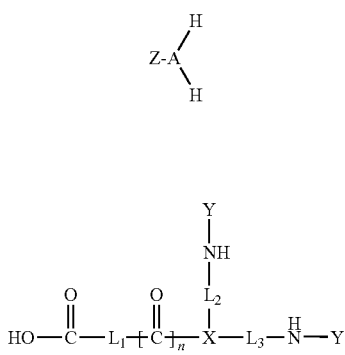

[Chemical Formula 3]

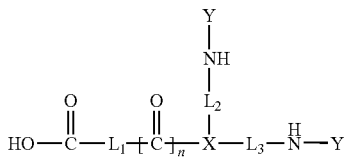

In the formulas, Z and A are defined as above in Chemical Formula (1);

$L_1$, $L_2$ and $L_3$ independently represent a chemical bond, or an alkylene having 1~10 carbon atom(s), wherein the carbon atoms in the alkylene may be further substituted by one or more oxygen atom(s);

X represents CH or N;

Y represents an amine protective group; and n is 0 or 1.

During the chemical reaction where the monomer having multi-amine functionality represented by Chemical Formula (3) is sequentially conjugated with a PNA oligomer, amine groups of the monomer having multi-amine functionality may be protected by conventional amine protective groups. Such protective groups include 9-fluorenylmethyl carbamate (Fmoc), t-butoxycarbonyl (Boc), trityl, benzyl, chloroacetyl, benzyloxycarbonyl, p-methoxybenzyloxycarbonyl, formyl, trifluoroacetyl, p-toluenesulfonyl, benzenesulfonyl, methanesulfonyl, p-nitrobenzyloxycarbonyl and 2,2,2-trichloroethoxycarbonyl.

Preferably in the monomer having multi-amine functionality of Chemical Formula (3), $L_1$, $L_2$ and $L_3$ independently represent a chemical bond, or —$CH_2$—, —$CH_2CH_2$—, —$CH_2CH_2CH_2$— or —$CH_2CH_2CH_2CH_2$—, X represents CH or N, and n is 0 or 1. Specific examples include the monomers represented by one of Chemical Formulas (3-1) to (3-3) protected by Fmoc functional groups, but are not limited thereto.

[Chemical Formula 3-1]

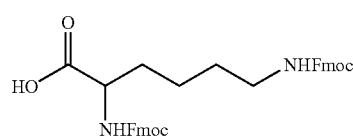

[Chemical Formula 3-2]

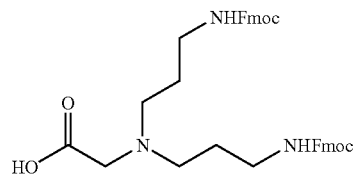

[Chemical Formula 3-3]

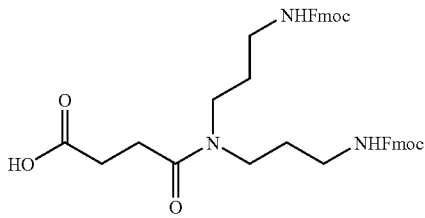

The PNA oligomer which is employed for the present invention can be synthesized from PNA monomer protected by benzothiazolesulfonyl (Bts) group according to the method of Korean Patent Registration No. 10-0464261; or from the PNA monomers protected by Fmoc or t-Boc [P. E. Nielsen (Ed.) "Peptide Nucleic Acids: Protocols and Applications" $2^{nd}$ Ed. (Horizon Bioscience, 2004)]. The scope of the present invention is not restricted by synthetic methods for PNA.

As can be shown in FIG. 1, the PNA conjugated with multi-amine linkers represented by Chemical Formula (1) according to the present invention is synthesized by sequentially conjugating a monomer containing one carboxyl group and two or more branched amine groups at least twice to the N-terminal of PNA oligomer or the N-terminal of the spacers conjugated to the PNA oligomer. The PNA according to the present invention is characterized by at least four amine groups at its terminal.

FIG. 1 schematically shows a solid support synthetic process for a PNA conjugated with multi-amine linkers according to the present invention. The synthetic process consists of three stages including deprotection process to remove the protective groups linked to the amine groups of the PNA oligomer; coupling or conjugation process wherein a monomer having multi-amine functionality is linked to a PNA oligomer; and capping process to remove the activity of the unreacted amine groups.

The first stage (deprotection process) is to remove the amine protective groups such as Fmoc, Boc or trityl, which protect amine terminal moieties of PNA, by a conventional process. Depending on the type of protective group, the process utilizes from 10 to 20% of piperidine solution in dimethylformamide (DMF) (in case of Fmoc protective group), or trifluoroacetic acid (TFA) solution in DMF or dichloromethane (in case of Boc or trityl protective group). By removing the amine protective groups, amine moieties are activated so that a monomer having multi-amine functionality can be linked thereto.

The second stage (coupling process) is to react the monomer having multi-amine functionality to the N-terminal of PNA to form an amide bond. The coupling process of the monomer having multi-amine functionality with PNA can be carried out by using a coupling agent conventionally used for peptide synthesis. Specific examples of the coupling agent include diisopropylcarbodiimide (DIC), dicyclohexylcarbodiimide, HATU, HOAt, HODhbt (L. A. Carpino et al., *Journal of American Chemical Society*, 1993, 115, 4397-4398), HAPyU, TAPipU (A. Ehrlich et al., *Tetrahedron Letters*, 1993, 4781-4784), HBTU (V. Dourtoglou et al., *Synthesis*, 1984, 572-574), TBTU, TPTU, TSTU, TNTU (R. Knorr et al., *Tetrahedron Letters*, 1989, 1927-1930), TOTU, BOP (B. Castro et al., *Tetrahedron Letters*, 1975, 1219-1222), PyBOP (J. Coste et al., *Tetrahedron Letters*, 1990, 205-208), BroP (J.

Coste et al., *Tetrahedron Letters,* 1990, 669-672), PyBroP (J. Coste et al., *Tetrahedron Letters,* 1991, 1967-1970), but are not restricted thereto.

The third stage (capping process) is to carry out capping the amine groups that might not have reacted with the monomer having multi-amine functionality during the coupling process, by using acetic anhydride, in order to prevent unnecessary reactions. Upon carrying out those three stages repeatedly, the number of amines increases with the number of repeated processes. If the reaction of linkage is repeated m times, the number of terminal amines is increased to $2^m$.

Finally, the PNA conjugated with multi-amine linkers prepared via those three stages is subjected to deprotection of amine protective group, and then is cleaved from solid support. The cleaved PNA conjugated with multi-amine linkers is immobilized on a solid surface and used for detection of nucleic acid or gene. PNA conjugated with multi-amine linkers may be used after purification.

PNA conjugated with multi-amine linkers according to the present invention is immobilized on a functionalized solid surface according to conventional method to immobilize on a solid surface by using terminal amine groups.

The solid substance is preferably selected from silica, silicon semiconductor, magnetic molecules, nylon, macromolecular compounds such as polydimethylsiloxane (PDMS), cellulose and nitrocellulose, but not restricted thereto. Further, the surface of the solid substance is functionalized by functional groups of aldehyde group, carboxylic group, epoxy group, isothiocyanate group, N-hydroxysuccinimidyl group or activated ester group. In the coupling reaction between amine terminal of PNA and the functional group on the solid surface, immobilization efficiency can be improved by using PNA conjugated with multi-amine linkers. Since the immobilization efficiency increases with the number of conjugation reactions with the monomer having multi-amine functionality, the number of monomer conjugation reaction is preferably from 2 to 10, more preferably from 2 to 7.

A nucleotide sequence detecting device or a gene diagnosis kit can be manufactured by immobilizing the PNA conjugated with multi-amine linkers on a functionalized surface of a solid substance. Those devices include, but are not restricted to, a PNA microarray wherein multiple PNA probes are arranged in two dimensions, PNA chips, PNA probes immobilized on the surface of microbeads having several μm size, a field-effect transistor using the PNA immobilized on silicon semiconductor or silicon nanowire, an impedance detector, a microcantilever, a surface acoustic wave sensor, or the like.

EXAMPLES

Now the present invention is illustrated in more detail by referring to specific examples. However, the present invention is not restricted by those examples, and it is apparent to a person having ordinary skill in the art that various alterations and modifications can be made within the spirit and scope of the invention.

Example 1

Synthesis of N,N-bis-[3-(9H-fluoren-9-yl-methoxycarbonylamino)propyl]succinamic acid (monomer compound of Chemical Formula 3-3)

As is shown in FIG. 2, bis(3-aminopropyl)amine was dissolved in methylene chloride (MC), and triethylamine (TEA) was added thereto in an amount of 2 molar equivalent of the bis(3-aminopropylamine). After cooling the mixture to 4° C., solution of Fmoc-N-hydroxysuccinimidyl ester (1.5 molar equivalent), dissolved in MC, was slowly added thereto over 30 minutes. To the mixture, 1 N HCl was added, and the resultant mixture was stirred for 50 minutes. White solid precipitate was isolated by filtration, and washed with MC to remove impurities and moisture. The solid obtained was dried with air blowing.

The dried solid was dissolved in MC and TEA, and succinic anhydride (1.2 molar equivalent) was added thereto, and the mixture was reacted with stirring for 30 minutes. The reaction mixture was washed with 1 N HCl to obtain organic layer, which was then dried over magnesium sulfate ($MgSO_4$). Purification via column chromatography using mixed solvent of MC and methanol (10:1) gave the title compound in 80% yield.

$^1$H NMR ($CDCl_3$, 300 MHz) δ 7.74 (d, 4H), 7.58 (t, 4H), 7.41-7.26 (m, 8H), 4.4-4.18 (m, 6H), 3.30-3.05 (m, 4H), 2.75-2.55 (m, 4H), 1.85-1.65 (m, 4H).

Examples 2-10

Synthesis of PNA Probes Conjugated with Multi-Amine Linkers

General Synthetic Process for PNA Oligomer

The PNA oligomer was synthesized via solid phase synthesis from a PNA monomer protected by Bts group and a functionalized resin, according to the process described in Korean Patent Registration No. 10-0464261. For the N-terminal, 8-amino-3,6-dioxaoctanoic acid (hereinafter, referred to as an eg linker) was conjugated twice as spacers. 8-(9H-fluoren-9-yl-methoxycarbonylamino)-3,6-dioxaoctanoic acid containing Fmoc as an amine protective group was employed as a monomer for the eg linker. The resin was used for the next reaction stage with PNA attached thereto.

General Synthetic Process for PNA Probes Conjugated with Multi-Amine Linkers a) The PNA attached to resin which was prepared as described above was treated with 10% piperidine solution in DMF for 20 minutes to remove Fmoc protective groups from the N-terminal, and washed three times with DMF.

b) Then, 1 equivalent of Bis Fmoc monomer (Compound of Chemical Formula (3-1), Chemical Formula (3-2) or Chemical Formula (3-3) prepared from Example 1), 1 equivalent of N-hydroxybenzotriazole (HOBt), 2 equivalents of diisopropylcarbodiimide, and DMF were added thereto. After agitating for 1 hour, the mixture was washed three times with DMF.

c) A DMF solution containing 5% acetic anhydride and 6% lutidin was added thereto. After agitating at ambient temperature for 5 minutes, the mixture was washed three times with DMF.

d) Step a) to c) described above was repeated as desired, and finally step a) was repeated to remove the Fmoc protective group.

e) The resin with PNA attached was treated with m-cresol/TFA (¼ v/v) solution for 2 hours, to remove PNA from the resin. Precipitate from treatment with ether was purified via HPLC to provide PNA compounds conjugated with multi-amine linkers of Examples 2 to 10.

TABLE 1

| Example | Probe | Base sequence (N→C) | N-terminal linker | Molecular weight |
|---|---|---|---|---|
| Ex. 2 | PNA2-1 | (eg)*₂-GCT GTT TGC TTT TAT T | None | 4621.4 |
| | PNA2-2 | (eg)₂-AGG CTG TTT GCT TTT ATT | | 5188.0 |
| | PNA2-3 | (eg)₂-GCT GTT TAT TTA TTA C | | 4614.4 |
| | PNA2-4 | (eg)₂-GGC TGT TTA TTT ATT ACA | | 5181.0 |
| Ex. 3 | PNA3-1 | (eg)₂-GCT GTT TGC TTT TAT T | Chemical Formula 1-1 | 5012.9 |
| | PNA3-2 | (eg)₂-AGG CTG TTT GCT TTT ATT | | 5579.5 |
| | PNA3-3 | (eg)₂-GCT GTT TAT TTA TTA C | | 5005.9 |
| | PNA3-4 | (eg)₂-GGC TGT TTA TTT ATT ACA | | 5572.5 |
| Ex. 4 | PNA4-1 | (eg)₂-GCT GTT TGC TTT TAT T | Chemical Formula 1-4 | 5519.7 |
| | PNA4-2 | (eg)₂-AGG CTG TTT GCT TTT ATT | | 6086.2 |
| | PNA4-3 | (eg)₂-GCT GTT TAT TTA TTA C | | 5512.7 |
| | PNA4-4 | (eg)₂-GGC TGT TTA TTT ATT ACA | | 6079.2 |
| Ex. 5 | PNA5-1 | (eg)₂-GCT GTT TGC TTT TAT T | Chemical Formula 1-2 | 5136.2 |
| | PNA5-2 | (eg)₂-AGG CTG TTT GCT TTT ATT | | 5702.7 |
| | PNA5-3 | (eg)₂-GCT GTT TAT TTA TTA C | | 5129.2 |
| | PNA5-4 | (eg)₂-GGC TGT TTA TTT ATT ACA | | 5695.7 |
| Ex. 6 | PNA6-1 | (eg)₂-GCT GTT TGC TTT TAT T | Chemical Formula 1-3 | 5262.3 |
| | PNA6-2 | (eg)₂-AGG CTG TTT GCT TTT ATT | | 5828.8 |
| | PNA6-3 | (eg)₂-GCT GTT TAT TTA TTA C | | 5255.3 |
| | PNA6-4 | (eg)₂-GGC TGT TTA TTT ATT ACA | | 5821.8 |
| Ex. 7 | PNA7-1 | (eg)₂-GAC ATT ACT CAC CCG | None | 4297.2 |
| | PNA7-2 | (eg)₂-GAC ATT AGT CAC CCG | | 4337.2 |
| Ex. 8 | PNA8-1 | (eg)₂-GAC ATT ACT CAC CCG | Chemical Formula 1-1 | 4688.7 |
| | PNA8-2 | (eg)₂-GAC ATT AGT CAC CCG | | 4728.7 |
| Ex. 9 | PNA9-1 | (eg)₂-GAC ATT ACT CAC CCG | Chemical Formula 1-2 | 4811.9 |
| | PNA9-2 | (eg)₂-GAC ATT AGT CAC CCG | | 4851.9 |
| Ex. 10 | PNA10-1 | (eg)₂-GAC ATT ACT CAC CCG | Chemical Formula 1-3 | 4938.1 |
| | PNA10-2 | (eg)₂-GAC ATT AGT CAC CCG | | 4978.1 |

*eg: 8-amino-3,6-dioxaoctanoic acid

Example 11-13

Manufacture of PNA Array Manufacture of PNA Array a) Diluting the purified PNA oligomer with 100 mM carbonate buffer solution (pH 10) containing sodium chloride (500 mM).

b) Spotting the PNA oligomers in a pin mode on a glass slide functionalized by epoxy group.

c) Standing the slide at ambient temperature while maintaining 75% of humidity for 4 hours.

d) Ultrasonic washing in DMF for 15 minutes.

e) Dipping the slide in DMF containing 0.1 M succinic anhydride, and storing at 40° C. for 2 hours.

f) Ultrasonic washing with DMF and deionized water, sequentially for 15 minutes.

g) Dipping the slide in 100 mM Tris-HCl containing 0.1 M ethanolamine, and storing at 40° C. for 2 hours.

h) Ultrasonic washing of the glass slide for 15 minutes twice with deionized water.

i) Treating the slide in boiling water for 5 minutes, and washing with deionized water for 5 minutes.

According to the manufacturing process for PNA array described above, PNA arrays of Examples 11 to 13 were manufactured.

In Example 11, the probes of Examples 2 to 4 (see Table 1) were diluted to a immobilization concentration of 50, 75 and 100 μM, and immobilized.

In Example 12, the probes of Examples 2, 3, 5 and 6 (see Table 1) were employed to manufacture the PNA arrays.

In Example 13, PNA array was manufactured by using the probes of Examples 7 to 10 (see Table 1). Employed were a slide whereon epoxy functional groups are exposed (manufactured by the inventors themselves) (Slide 1); a slide from Company A whereon aldehyde groups are exposed (Slide 2); a commercial slide whereon epoxy groups are exposed (Slide 3); a commercial slide from Company B, prepared by treating an amine slide with butandiol diglycidylether (Slide 4); a commercial slide from Company C, prepared by treating an amine slide with 1,4-phenylene diisothiocyanate (Slide 5); and a commercial slide from Company D whereon activated ester groups are exposed (Slide 6).

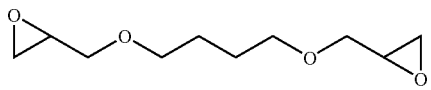

Butanediol diglycidyl ether

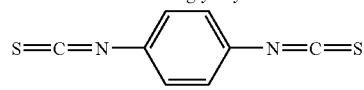

1,4-phenylenediisothiocyanate

Example 14-15

Determination of Immobilization Efficiency of PNA Array Hybridized with DNA Oligomer In order to compare the degree of immobilization of probes on the PNA array manufactured according to Example 11, DNA oligomers labeled by Cy3 fluorescent material at 5'-terminal [see Table 2] were hybridized, and the intensity of fluorescence was compared.

TABLE 2

| Type | Base sequence (5'→3') | Length (number of bases) | Labeler (5'-terminal) |
|---|---|---|---|
| Target DNA oligomer 1* | CTC TAA TAA AAG CAA ACA GCC TG | 23 | Cy3 |
| Target DNA oligomer 2** | CTG TAA TAA ATA AAC AGC CTG | 21 | Cy3 |

*Target DNA oligomer 1 was designed to specifically hybridize with PNA oligomers 2-1, 2-2, 3-1, 3-2, 4-1, 4-2, 5-1, 5-2, 6-1 and 6-2 of Examples 2 to 6.
**Target DNA oligomer 2 was designed to specifically hybridize with PNA oligomers 2-3, 2-4, 3-3, 3-4, 4-3, 4-4, 5-3, 5-4, 6-3 and 6-4.

Hybridization Process of Synthetic DNA Oligomer a) A silicon rubber sealing mat manufactured to contain 100 µl of hybridization solution was adhered to a PNA array.

b) The target DNA oligomer was diluted with 100 mM Tris-buffer (pH 7.6) containing sodium chloride (150 mM).

c) To the well formed in the silicon rubber sealing mat to which the PNA array has been adhered, buffer solution (100 µl), in which the target DNA oligomer has been diluted, is added.

d) Hybridization reaction is carried out at 40° C. for 2 hours.

e) After removing the silicon rubber sealing mat on it, the PNA array is washed twice with 10 mM phosphate buffer solution for 5 minutes.

f) The PNA array is dried.

g) Intensity of fluorescence is measured by using a fluorescence microarray scanner.

In Example 14, the PNA array manufactured according to Example 11 was hybridized with target DNA oligomer 1 (Sequence ID No. 1) and target DNA oligomer 2 (Sequence ID No. 1), according to the hybridization process described above, and the intensity of fluorescence was shown in FIGS. 3 to 5.

FIG. 3 shows the results of hybridization of labeled target DNA oligomer 1 (Sequence ID No. 1) with the PNA array from Example 11. The fluorescence emitted from spots of probes PNA 4-1 and 4-2 (complimentary base sequences) was more intense than that from spots of probes PNA 4-3 and 4-4 (noncomplementary base sequences). Further, the fluorescence emitted from spots of probes PNA 3-1 and 3-2 (complimentary base sequences) was more intense than that from spots of probes PNA 3-3 and 3-4 (noncomplementary base sequences). When the base sequences of the PNA probes are identical, the intensity of fluorescence signal increases in the order of probes PNA 2-1, 3-1 and 4-1. In case of probes PNA 2-2, 3-2 and 4-2, the intensity of fluorescence signal increases in the order. Since this order corresponds to the number of amine groups at the terminal of PNA probes (1, 4, 8 in the order) used for immobilization, it is concluded that the intensity of detection signal increases with the increase of the number of terminal amine groups.

From FIG. 4 which shows the results of hybridization of labeled target DNA oligomer 2 (Sequence ID No. 2) and the PNA array from Example 11, the conclusion is the same as described above. The intensity of fluorescence emitted from spots of probes PNA 4-3 and 4-4 (complimentary base sequences) was higher than that from spots of probes PNA 4-1 and 4-2 (noncomplementary base sequences). Further, the intensity of fluorescence emitted from spots of probes PNA 3-3 and 3-4 (complimentary base sequences) was higher than that from spots of probes PNA 3-1 and 3-2 (noncomplementary base sequences). When the base sequences of the PNA probes are identical, the fluorescence signal increases in the order of probes PNA 2-3, 3-3 and 4-3. In case of probes PNA 2-4, 3-4 and 4-4, the intensity of fluorescence signal increases in the order. Since this order corresponds to the number of amine groups at the terminal of PNA probes (1, 4, 8 in the order) used for immobilization, it is concluded that the intensity of detection signal increases with the increase with the increase of the number of terminal amine groups.

As shown on the scanned image of PNA array in FIG. 5, the fluorescence signal increases in the order of probes PNA 2-1, 3-1 and 4-1; and in the order of PNA 2-3, 3-3 and 4-3.

In Example 15, the target DNA oligomer 2 (Sequence ID No. 2) was hybridized with the PNA array from Example 12 by using the hybridization process described above. The results are shown in FIGS. 6 and 7.

FIG. 6 shows the results of intensity of fluorescence measured after hybridization of labeled target DNA oligomer 2 (Sequence ID No. 2) and the PNA array from Example 12. The fluorescence emitted from spots of probes PNA 2-3 and 2-4 (complimentary base sequences) was more intense than that from spots of probes PNA 2-1 and 2-2 (noncomplementary base sequences); and the fluorescence emitted from spots of probes PNA 3-3 and 3-4 (complimentary base sequences) was more intense than that from spots of probes PNA 3-1 and 3-2 (noncomplementary base sequences). Further, the fluorescence emitted from spots of probes PNA 5-3 and 5-4 (complimentary base sequences) was more intense than that from spots of probes PNA 5-1 and 5-2 (noncomplementary base sequences); and the fluorescence emitted from spots of probes PNA 6-3 and 6-4 (complimentary base sequences) was more intense than that from spots of probes PNA 6-1 and 6-2 (noncomplementary base sequences).

It is also found that the fluorescence emitted from spots of probes PNA 3-3, 3-4, 5-3, 5-4, 6-3 and 6-4 having four amine groups was more intense than that from spots of probes PNA 2-3 and 2-4 having only one amine.

FIG. 7 shows the perfect match/mismatch signal ratio (P/M ratio) of the fluorescence signal measured after hybridization of the PNA array from Example 12 with labeled target DNA oligomer 2 (Sequence ID No. 2). If the number of amine group at the terminal of PNA probe is one (1), P/M ratio shows the value in the range of 7-8 (PNA 2-3/PNA 2-1, PNA 2-4/PNA 2-2). Whereas, when the number of amine group at the terminal of PNA probe is four (4), all P/M ratios are more than 10, with a maximum of 35 (PNA 5-3/PNA 5-1). Accordingly, it is concluded that use of PNA conjugated with multi-amine linkers enhances specificity as well as intensity of detection signal.

Probe PNA 3-1 and probe PNA 5-1 have identical PNA base sequence but different multi-amine linkers. Though there are the same number of amine groups, the four amine groups are equidistant from a branch point in probe PNA 5-1, whereas they are not in probe PNA 3-1. Likewise, though the base sequence and the number of amine groups are the same for probes PNA 3-3 and 5-3, the four amine groups are equidistant from a branch point in probe PNA 5-3, whereas they are not in probe PNA 3-3.

FIG. 8 shows the results of hybridization of probes PNA 3-1 and 5-1 with DNA oligomer 1 (Sequence ID No. 1) (a complimentary base sequence) in different concentrations, and the results of hybridization of probes PNA 3-3 and 5-3 with DNA oligomer 2 (Sequence ID No. 2) (a complimentary base sequence) in different concentrations. It is found that probes PNA 5-1, 5-3 having equidistant amine groups from a branch point exhibited more intense signal than probes PNA 3-1 and 3-3 having non-equidistant amine groups from a branch point (FIG. 8).

Example 16

PNA-DNA Hybridization by Using *E. coli* Polymerase Chain Reaction Product

DNA was amplified by using 16S rDNA gene of *E. coli* as a template. DNA of *E. coli* was extracted by using a DNA extraction kit (Qiagen), and a synthesized DNA oligomer having the base sequence shown in Table 3 was employed as a primer for polymerase chain reaction (PCR). A PCR solution having the composition as shown in Table 4 was prepared, and subjected to PCR according to the process listed in Table 5.

TABLE 3

PCR primer

| PCR primer | Base sequence (5'→3') | labeler (5'-terminal) |
|---|---|---|
| ECb49F | TGC AAG TCG AAC GGT AAC AG | Biotin |
| ECb182R | TGC GAC GTT ATG CGG TAT TA | Biotin |

TABLE 4

PCR solution

| Composition | Polymerase | Buffer | dNTP mixture | BSA | ECb 49F | ECb 182R | Sterilized distilled water | DNA |
|---|---|---|---|---|---|---|---|---|
| Concentration | 5 U/μL | 10X | 25 mM | 2% | 20 pM | 20 pM | — | — |
| Amount (μL) | 0.2 | 5 | 1 | 5 | 1 | 1 | 29 | 8 |

TABLE 5

PCR amplification process

| No. of repeat | Once | 30 times repeated | | | Once |
|---|---|---|---|---|---|
| Condition | 94° C., 5 min | 94° C., 30 sec | 55° C., 30 sec | 72° C., 30 sec | 72° C., 10 min |

PNA-DNA Hybridization Process by Means of PCR Product

An aliquot of the PCR product (5 μl) taken was treated at 94° C. for 5 minutes, and mixed with 50 mM phosphate buffer solution containing sodium chloride (500 mM). To the mixture, 1 mg/mL of Cy5-streptavidin (0.6 μl) was added. After thorough mixing, the mixture was added to the PNA array by using an epoxy slide manufactured by the inventors according to Example 13. The resultant mixture was subjected to hybridization at 40° C. for 2 hours. The reaction mixture was washed twice with 10 mM phosphate buffer for 5 minutes and dried.

The PNA arrays obtained from PNA-DNA hybridization as described above were compared in intensity of fluorescence emitted from the spots of the probes immobilized on each slide, by means of a fluorescence microarray scanner. The results are shown in FIGS. 9 and 10.

In probes PNA 7-1, 8-1, 9-1, 10-1, the sequences of 15 nucleobase are identical, but the number of terminal amine groups are different. PNA 7-1 has one terminal amine group, whereas probes PNA 8-1, 9-1 and 10-1 have four amine groups at the terminal. In probes PNA 7-2, 8-2, 9-2 and 10-2, the sequence of 15 bases are identical, but only one base at the center is different from the base sequences of probes PNA 7-1, 8-1, 9-1 and 10-1.

The signal of probes PNA 8-1, 9-1 and 10-1 having four terminal amine groups is far more intense than that of probe PNA 7-1 having only one terminal amine group. Probes PNA 8-2, 9-2 and 10-2 having single mismatch base at the center among the 15 bases show little fluorescence signal. The signal of PNA array with probes PNA 8-1, 9-1 and 10-1 having four amine groups are very specific (FIG. 9).

The PNA conjugated with the multi-amine linkers is also effective on a slide with other functional groups than epoxy groups. As can be seen from FIG. 10, for the slides prepared by treating an epoxy slide (slide 1, 3) and an amine slide treated with butanediol diglycidylether (Slide 4), the PNA probes conjugated with multi-amine linkers exhibited far more intense signal than the PNA probes having single amine group. For a slide whereon activated ester group is exposed (Slide 6), the PNA conjugated with multi-amine linkers exhibited more intense detection signal than the PNA containing single amine group. In case of an aldehyde slide (Slide 2) and a slide prepared by treating an amine slide with 1,4-phenylene diisothiocyanate (Slide 5), the PNA conjugated with multi-amine linkers exhibited similar intensity of detection signals to that of the PNA containing single amine group.

INDUSTRIAL APPLICABILITY

As is shown from the specific embodiments, the PNA conjugated with multi-amine linkers according to the present invention comprises linkers prepared by conjugating monomers having multi-amine functionality at the N-terminal of PNA, so that the PNA can be effectively immobilized on a solid surface. Thus, by using the PNAs, intensity of detection signal of target nucleic acid, sensitivity and specificity of a nucleotide sequence detecting device and a kit for gene diagnosis can be improved.

The PNA conjugated with multi-amine linkers can be immobilized on a functionalized plastic substrate, microbeads, membrane, a semiconductor substrate, or the like, as well as a functionalized glass substrate, and used for extensive applications.

The invention claimed is:

1. A peptide nucleic acid (PNA) conjugated with multi-amine linkers, which is represented by Chemical Formula (1):

[Chemical Formula 1]

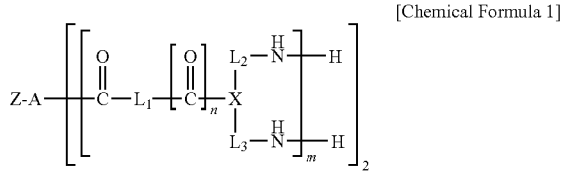

wherein in the Formula, Z represents a PNA oligomer having 8-30 nucleobases;

wherein A is bonded to N-terminal of the PNA oligomer and is optional, and when present represents

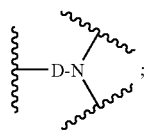

wherein D represents alkylene having 8-200 carbon atoms, and one or more carbon atoms of alkylene may be substituted by nitrogen, oxygen or carbonyl;

$L_1$, $L_2$ and $L_3$ independently represent a chemical bond, or an alkylene having 1-10 carbon atom(s), wherein the carbon atoms in the alkylene may be further substituted by one or more oxygen atom(s);

X represents CH or N;

m represents an integer from 2 to 10; and n is 0 or 1.

2. A PNA conjugated with multi-amine linkers according to claim 1, wherein $L_1$ is a chemical bond, $L_2$ and $L_3$ independently represent —$CH_2CH_2CH_2CH_2$—, X is CH, m is an integer from 2 to 7, and n is 0, in Chemical Formula (1).

3. A PNA conjugated with multi-amine linkers according to claim 1, wherein $L_1$ is —$CH_2$—, $L_2$ and $L_3$ independently represent —$CH_2CH_2CH_2$—, X is N, m is 2 or 3, and n is 0, in Chemical Formula (1).

4. A PNA conjugated with multi-amine linkers according to claim 1, wherein $L_1$ is —$CH_2CH_2$—, $L_2$ and $L_3$ represent —$CH_2CH_2CH_2$—, X is N, m is 2 or 3, and n is 1, in Chemical Formula (1).

5. A PNA conjugated with multi-amine linkers according to claim 1, wherein A in Chemical Formula (1) is selected from the structures represented by one of the following chemical formulas:

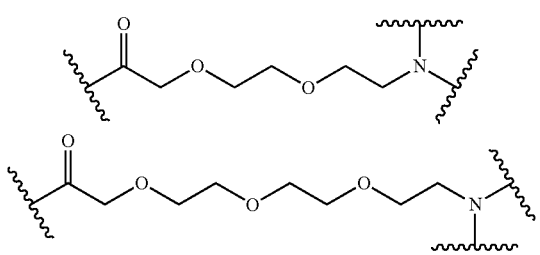

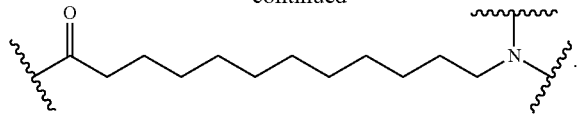

6. A method to prepare a PNA conjugated with multi-amine linkers, the method comprising:

sequentially reacting a monomer (Chemical Formula 3) having multi-amine protected functionality, with a PNA oligomer derivative (Chemical Formula 2) to obtain the PNA (Chemical Formula 1) wherein the multi-amine linkers have been conjugated,

[Chemical Formula 1]

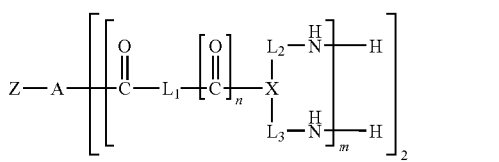

[Chemical Formula 2]

[Chemical Formula 3]

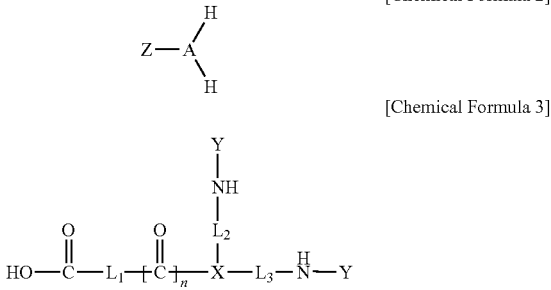

wherein in the Formulas, Z represents a PNA oligomer having 8-30 nucleobases;

wherein A is bonded to N-terminal of the PNA oligomer and is optional, and when present represents

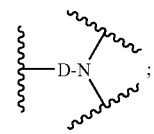

wherein D represents alkylene having 8-200 carbon atoms, and one or more carbon atoms of alkylene may be substituted by nitrogen, oxygen or carbonyl;

$L_1$, $L_2$ and $L_3$ independently represent a chemical bond, or an alkylene having 1~10 carbon atom(s), wherein the carbon atoms in the alkylene may be further substituted by one or more oxygen atom(s);

X represents CH or N;

Y represents an amine protective group;

m represents an integer from 2 to 10; and n is 0 or 1.

7. A method to prepare a PNA conjugated with multi-amine linkers according to claim 6, wherein the amine protective group (Y) in Chemical Formula (3) is selected from the group consisting of Fmoc, t-butoxycarbonyl (Boc), trityl, benzyl, chloroacetyl, benzyloxycarbonyl, p-methoxybenzyloxycarbonyl, formyl, trifluoroacetyl, p-toluenesulfonyl, benzenesulfonyl, methanesulfonyl, p-nitrobenzyloxycarbonyl and 2,2,2-trichloroethoxycarbonyl.

8. A method to immobilize PNA conjugated with multi-amine linkers according to claim 1 on a solid surface whereon an aldehyde group, carboxylic group, epoxy group, isothiocyanate group, N-hydroxysuccinimidyl group or activated ester group (NHS) is exposed.

9. A method to immobilize according to claim 8, wherein the solid is selected from the group consisting of glass substrate, plastic substrate, silica, silicon semiconductor, magnetic molecules, nylon, macromolecular compounds such as polydimethylsiloxane (PDMS), cellulose and nitrocellulose.

10. A nucleic acid detecting device comprising PNA conjugated with multi-amine linkers according to claim 1.

11. A nucleic acid detecting device according to claim 10, which is selected from the group consisting of PNA microarrays, PNA chips, PNA field-effect transistors, impedance detectors, microcantilever and surface acoustic wave sensors.

12. A kit for gene diagnosis comprising PNA conjugated with multi-amine linkers according to claim 1.

13. A kit for gene diagnosis comprising PNA conjugated with multi-amine linkers, which is manufactured by using the immobilization method according to claim 8.

* * * * *